US012594015B2

(12) United States Patent (10) Patent No.: US 12,594,015 B2
Gatoro et al. (45) Date of Patent: Apr. 7, 2026

(54) BLOOD DRAW DEVICE WITH NON-CONTACT ADVANCEMENT DEVICE

(71) Applicant: Becton, Dickinson and Company, Franklin Lakes, NJ (US)

(72) Inventors: Arnold Gatoro, Salt Lake City, UT (US); Megan S. Scherich, Salt Lake City, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 420 days.

(21) Appl. No.: 18/237,169

(22) Filed: Aug. 23, 2023

(65) Prior Publication Data

US 2024/0065593 A1 Feb. 29, 2024

Related U.S. Application Data

(60) Provisional application No. 63/400,498, filed on Aug. 24, 2022.

(51) Int. Cl.
*A61B 5/15* (2006.01)
*A61M 25/06* (2006.01)
(52) U.S. Cl.
CPC ... *A61B 5/150992* (2013.01); *A61M 25/0606* (2013.01)
(58) Field of Classification Search
CPC ............ A61B 5/150992; A61B 5/1513; A61B 5/150389; A61B 5/150404; A61B 5/150519; A61B 5/153
See application file for complete search history.

(56) References Cited

U.S. PATENT DOCUMENTS

| | | | |
|---|---|---|---|
| 5,360,417 A | 11/1994 | Gravener et al. | |
| 9,445,868 B2 | 9/2016 | Hull et al. | |
| 11,173,277 B2 * | 11/2021 | Burkholz | A61M 25/0017 |
| 2021/0213245 A1 | 7/2021 | Burkholz et al. | |
| 2021/0299426 A1 * | 9/2021 | Scherich | A61B 5/150992 |
| 2022/0218955 A1 | 7/2022 | Scherich et al. | |

FOREIGN PATENT DOCUMENTS

| | | |
|---|---|---|
| WO | 2018/152059 A1 | 8/2018 |
| WO | 2021/141766 A1 | 7/2021 |
| WO | 2021/141774 A1 | 7/2021 |
| WO | 2022/155181 A1 | 7/2022 |

* cited by examiner

*Primary Examiner* — May A Abouelela
*Assistant Examiner* — Yasmeen S Warsi
(74) *Attorney, Agent, or Firm* — The Webb Law Firm

(57) ABSTRACT

Provided herein is a blood draw device that includes an introducer having a housing with a guide tube fixedly contained therein that defines as guide lumen. A catheter arrangement moveable within the guide lumen includes a catheter defining a first catheter lumen, a secondary catheter defining a second catheter lumen, and a catheter fitting coupled between the catheter and the secondary catheter to fluidly connect the first and second catheter lumens. An advancement member moveable along the introducer in the lengthwise direction includes an arrangement of pinch members positioned within the housing configured to pinch the guide tube and to move along the guide tube when the advancement member is moved. In response to moving the advancement member distally along the housing, the pinch members push the catheter fitting distally within the guide lumen, such that the catheter and secondary catheter are also advanced distally.

20 Claims, 8 Drawing Sheets

BLOOD DRAW DEVICE WITH NON-CONTACT ADVANCEMENT DEVICE

CROSS-REFERENCE TO RELATED APPLICATION

The present application claims priority to U.S. Provisional Application No. 63/400,498, entitled "Blood Draw Device with Non-Contact Advancement Device", filed Aug. 24, 2022, the entire disclosure of which is hereby incorporated by reference in its entirety.

BACKGROUND OF THE INVENTION

Field of the Invention

Provided herein are devices and components for use in vascular access, and, in particular, devices and components for use with blood draw through indwelling catheters.

Description of Related Art

Catheters are frequently utilized to administer fluids into and out of the body. Patients in a variety of settings, including in hospitals and in home care, receive fluids, pharmaceuticals, and blood products via a vascular access device (VAD) that includes such a catheter inserted into a patient's vascular system. A common VAD includes a plastic catheter that is inserted into a patient's vein, with a length of the catheter varying from a few centimeters when the VAD is a peripheral intravenous catheter (PIVC) to many centimeters when the VAD is a central venous catheter (CVC), as examples.

Recent developments in the PIVC field have led to the emergence of technologies designed to facilitate blood draw using an in-dwelling PIVC and accompanying blood draw device. These blood draw devices have focused on the ability to reliably collect a high-quality blood sample and reduce hemolysis. The main method by which these devices work is by employing an introducer for inserting a catheter, probe, tube, or other instrument through the catheter lumen of the PIVC, with the introducer being attached to a catheter adapter of the PIVC that provide for insertion of the catheter. For example, the catheter adapter may include a needleless access connector thereon by which the catheter may be introduced to provide access to the PIVC and into the patient's vasculature. A syringe or vacutainer may then be used to collect blood samples without needing to subject the patient to additional needle sticks.

The introducer of a blood draw device typically includes a housing, a catheter movable within the housing so as to be extendable out therefrom for advancement into the in-dwelling PIVC, and an advancement member that may be actuated by an operator relative to the housing. That is, the advancement member may be moved distally by the operator to cause a corresponding movement of the catheter relative to the housing, such that the catheter may be advanced out from the housing and into the in-dwelling PIVC. However, during deployment of the catheter of the blood draw device, especially when the proximal end portion of the catheter reaches a curved region of the PIVC (near where the PIVC enters the skin) and is caused to curve back and forth as it passes along the vein, the catheter of the blood draw device is subject to a column load which can cause bending, kinking, and/or deformation of the catheter.

As the catheter bends, any additional force applied thereto can then cause the catheter to double back on itself and collapse.

Another issue associated with the use of existing blood draw devices with an in-dwelling PIVC is the potential for the introduction of microbes into the PIVC fluid path, which can lead to catheter-related blood stream infections (CRB-SIs). That is, the introduction and retraction of a catheter or other instrument into and out of the PIVC using existing introducers may introduce microbes into the PIVC fluid path.

Accordingly, a need exists in the art for a blood draw device and introducer thereof that provides for advancement of a catheter into the PIVC while minimizing the potential for bending, kinking, or deformation of the catheter. A need also exists in the art for a blood draw device and introducer thereof that provides additional barriers against the introduction of microbes into the PIVC fluid path.

SUMMARY OF THE INVENTION

Provided herein is a blood draw device for use with a peripheral intravenous catheter (PIVC). The blood draw device includes an introducer having a housing extending in a lengthwise direction between a proximal end and a distal end and a guide tube fixedly contained within the housing and extending in the lengthwise direction, the guide tube defining a guide lumen. The blood draw device also includes a catheter arrangement moveable within the guide lumen, the catheter arrangement having a catheter defining a first catheter lumen and having a proximal end and a distal end, a secondary catheter defining a second catheter lumen and having a proximal end and a distal end, and a catheter fitting coupled between the proximal end of the catheter and the distal end of the secondary catheter, to fluidly connect the first and second catheter lumens. The blood draw device further includes an advancement member coupled to the introducer and moveable in the lengthwise direction, the advancement member comprising an arrangement of pinch members positioned within the housing that is configured to pinch the guide tube and to move along the guide tube when the advancement member is moved. In response to moving the advancement member distally along the housing, the arrangement of pinch members push the catheter fitting distally within the guide lumen, such that the catheter and secondary catheter are also advanced distally.

In some embodiments, the advancement member includes a push tab positioned on an outer surface of the housing and actuatable by a user to move in the lengthwise direction and a main body joined to the push tab via a connecting portion, the main body positioned within an interior volume of the housing and including a channel formed therethrough to receive the guide tube, with the arrangement of pinch members integrated with the main body. The connecting portion is seated within a groove in the housing that extends in the lengthwise direction, and wherein the connecting portion is slideable within the groove to enable movement of the advancement member in the lengthwise direction.

In some embodiments, the arrangement of pinch members includes a plurality of bearings seated within recesses or cavities formed in the main body, the plurality of bearings extending into the channel to pinch the guide tube.

In some embodiments, the arrangement of pinch members includes a plurality of protrusions formed as part of the main body and that extend into the channel to pinch the guide tube, the plurality of protrusions comprising spherical or cylindrical protrusions.

In some embodiments, the arrangement of pinch members is configured such that at least one pinch member of the arrangement of pinch members is positioned on each of opposing ends of the catheter fitting, to trap the catheter fitting therebetween.

In some embodiments, the guide tube is a flexible material that deflects or bends when pinched by the arrangement of pinch members.

In some embodiments, the guide tube includes a lubricant applied to the guide lumen, to facilitate movement of the catheter arrangement within the guide lumen.

In some embodiments, the guide tube supports movement of the catheter arrangement through the guide lumen along a full length of the housing during lengthwise movement of the advancement member, so as to prevent kinking of the catheter.

In some embodiments, the catheter fitting includes a fitting body having a first end engageable with the proximal end of the catheter and a second end engageable with the distal end of the secondary catheter, the fitting body having a hollow structure that enables fluid flow between the catheter and the secondary catheter. The fitting body includes a plurality of seats that engage the arrangement of pinch members, through the guide tube, such that the catheter fitting is pushed within the guide lumen in response to movement of the advancement member along the housing.

In some embodiments, the housing includes an end wall at the proximal end of the housing, the end wall including an opening formed therein that receives the secondary catheter and provides for movement of the secondary catheter relative to the housing.

In accordance with one aspect, the catheter and secondary catheter are advanced distally, via the arrangement of pinch members pushing the catheter fitting within the guide lumen, without direct contact between the advancement member and the catheter arrangement.

In accordance with one aspect, in response to moving the advancement member proximally along the housing, the arrangement of pinch members push the catheter fitting proximally within the guide lumen, such that the catheter and secondary catheter are also retracted proximally.

Another blood draw device for use with a PIVC is provided that includes an introducer having a housing extending in a lengthwise direction between a proximal end and a distal end and a guide tube fixedly contained within the housing and extending in the lengthwise direction, the guide tube defining a guide lumen. The blood draw device also includes a catheter arrangement moveable within the guide lumen, the catheter arrangement having a catheter defining a first catheter lumen and having a proximal end and a distal end, a secondary catheter defining a second catheter lumen and having a proximal end and a distal end, and a catheter fitting coupled between the proximal end of the catheter and the distal end of the secondary catheter, to fluidly connect the first and second catheter lumens. The blood draw device further includes an advancement member configured to move along the housing in the lengthwise direction and, responsive to such movement, distally advance or proximally retract the catheter arrangement in a contactless manner. The advancement member comprises an arrangement of pinch members positioned within the housing that are configured to pinch the guide tube and to push the catheter fitting within the guide lumen when the advancement member is moved, thereby distally advancing or proximally retracting the catheter and the secondary catheter.

In some embodiments, the arrangement of pinch members is configured such that at least one pinch member of the arrangement of pinch members is positioned on each of opposing ends of the catheter fitting, to trap the catheter fitting therebetween.

In some embodiments, the advancement member includes a push tab positioned on an outer surface of the housing and actuatable by a user to move in the lengthwise direction and a main body joined to the push tab via a connecting portion, the main body positioned within an interior volume of the housing and including a channel formed therethrough to receive the guide tube, with the arrangement of pinch members integrated with the main body. The connecting portion is seated within a groove in the housing that extends in the lengthwise direction, and wherein the connecting portion is slideable within the groove to enable movement of the advancement member in the lengthwise direction.

In some embodiments, the arrangement of pinch members includes a plurality of bearings seated within recesses or cavities formed in the main body, the plurality of bearings extending into the channel to pinch the guide tube.

In some embodiments, the arrangement of pinch members includes a plurality of protrusions formed as part of the main body and that extend into the channel to pinch the guide tube, the plurality of protrusions comprising spherical or cylindrical protrusions.

In some embodiments, the catheter fitting includes a fitting body having a first end engageable with the proximal end of the catheter and a second end engageable with the distal end of the secondary catheter, the fitting body having a hollow structure that enables fluid flow between the catheter and the secondary catheter. The fitting body includes a plurality of seats that engage the arrangement of pinch members, through the guide tube, such that the catheter fitting is pushed within the guide lumen in response to movement of the advancement member along the housing.

In some embodiments, the guide tube includes a lubricant applied to the guide lumen, to facilitate movement of the catheter arrangement within the guide lumen.

In accordance with one aspect, the guide tube supports movement of the catheter arrangement through the guide lumen along a full length of the housing during lengthwise movement of the advancement member, so as to prevent kinking of the catheter during advancing or retracting thereof.

DESCRIPTION OF THE INVENTION

Figure 1:
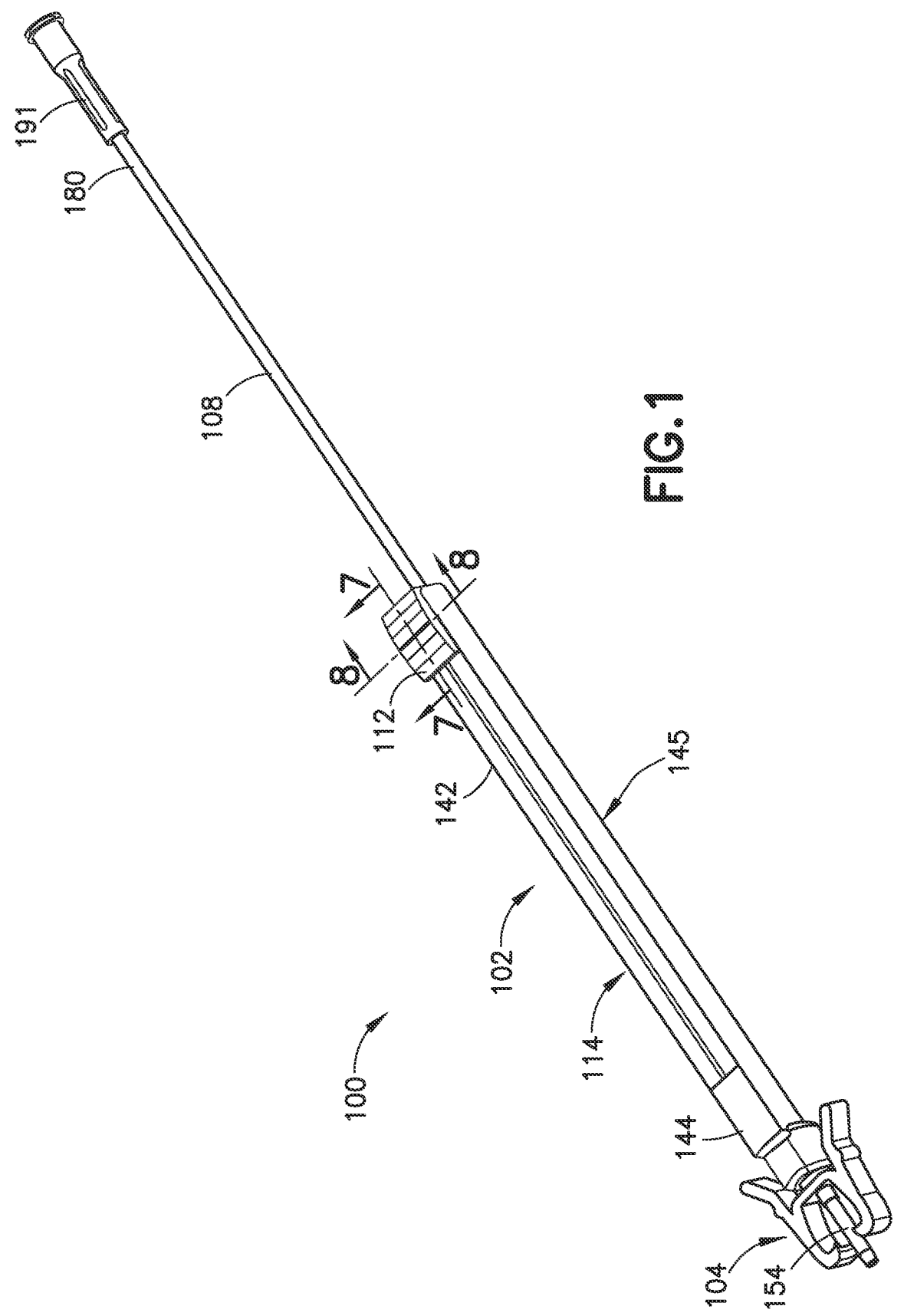
FIG. 1 is a perspective view of a blood draw device with which embodiments of the present application may incorporated.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

Spatial or directional terms, such as "left", "right", "inner", "outer", "above", "below", and the like, are not to be considered as limiting as the invention can assume various alternative orientations.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

The terms "first", "second", and the like are not intended to refer to any particular order or chronology, but refer to different conditions, properties, or elements.

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

FIGS. 1-10 illustrate a blood draw device 100 (and differing configurations in which it is operated) cording to embodiments of the present disclosure. The blood draw device 100 can be any suitable shape, size, or configuration and can be coupled to a PIVC or other catheter (not shown in FIGS. 1-14), for example, via a lock and/or adapter. As described in further detail herein, a user can transition the blood draw device 100 from a first configuration to a second configuration to advance a catheter through an existing, placed, and/or indwelling NYC when the blood draw device 100 is coupled thereto) such that at least an end portion of the catheter is disposed in a distal position relative to the PIVC. Moreover, with peripheral intravenous lines each having a shape, size, and/or configuration that can vary based on, for example, a manufacturer of the PIVC and/or its intended usage, the blood draw device 100 can be arranged to allow the blood draw device 100 to be coupled to a PIVC having any suitable configuration and subsequently, to advance at least a portion of a catheter through the PIVC. In addition, the blood draw device 100 can be manipulated by a user to place a distal surface of the catheter a predetermined and/or desired distance beyond a distal surface of the PIVC to be disposed within a portion of a vein that receives a substantially unobstructed flow of blood.

Figure 2:
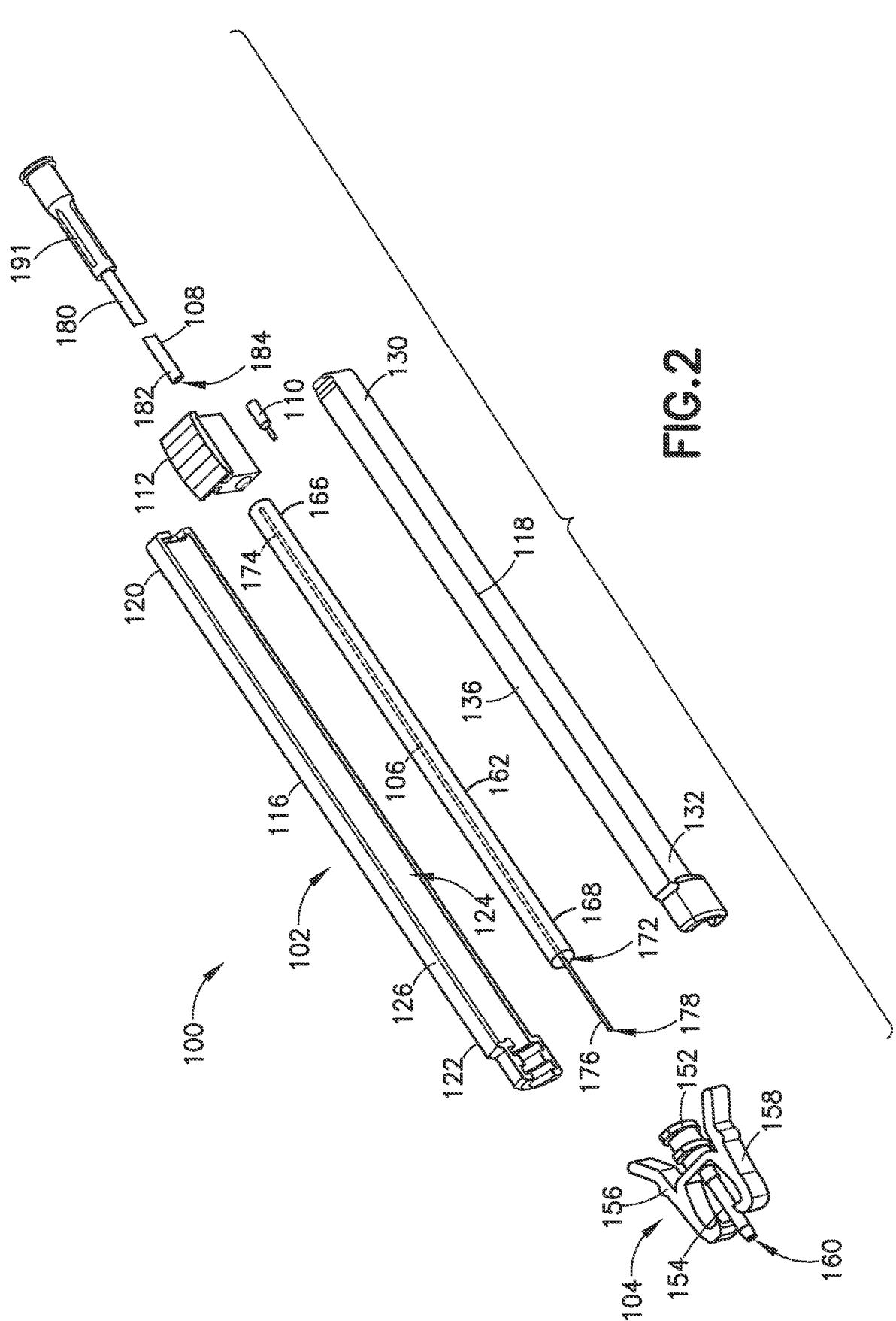
FIG. 2 is an exploded view of the blood draw device of FIG. 1.

As shown in FIGS. 1 and 2, the blood draw device 100 includes an introducer 102, a lock 104, a catheter 106, a secondary catheter 108, a catheter fitting 110, and an advancement member 112. The introducer 102 can be any suitable shape, size, or configuration. For example, in some embodiments, the introducer 102 can be an elongated member having a substantially circular cross-sectional shape. In some embodiments, the shape of the introducer 102 and/or one or more features or surface finishes of at least an outer surface of the introducer 102 can be arranged to increase the ergonomics of the blood draw device 100, which in some instances, can allow a user to manipulate the blood draw device 100 with one hand (i.e., single-handed use).

As shown in FIGS. 1-6, the introducer 102 of the blood draw device 100 includes an introducer housing 114 having a first housing member 116 and a second housing member 118 that are coupled to collectively form the housing 114. While introducer housing 114 is shown as being formed from first housing member 116 and second housing member 118, it is recognized that the introducer housing 114 could be formed as a single, integral structure according to other embodiments.

The first housing member 116 includes a proximal end portion 120, a distal end portion 122, an inner surface 124, and a top surface 126. The proximal end portion 120 of the first housing member 116, and more specifically, a proximal wall of the first housing member 116, defines a notch 128 configured to selectively receive a portion of the secondary catheter 108, as described in further detail herein.

The second housing member 118 has a proximal end portion 130, a distal end portion 132, an inner surface 134, and a top surface 136. As described above with reference to the first housing member 116, the proximal end portion 130 of the second housing member 118, and more specifically, a proximal wall of the second housing member 118 defines a notch 138 configured to selectively receive a portion of the secondary catheter 108.

As described in further detail herein, a portion of the advancement member 112 is configured to be advanced along the introducer housing 114 as a user moves the advancement member 112 relative to the introducer housing 114. Movement of the advancement member 112 distally along the introducer housing 114 facilitates the advancing of a tube or catheter arrangement 140 (comprised of catheter 106, secondary catheter 108, and catheter fitting 110) through a portion of the blood draw device 100, such that the catheter 106 may be advanced into a portion of the PIVC and/or a portion of the vasculature.

Figures 5, 6:
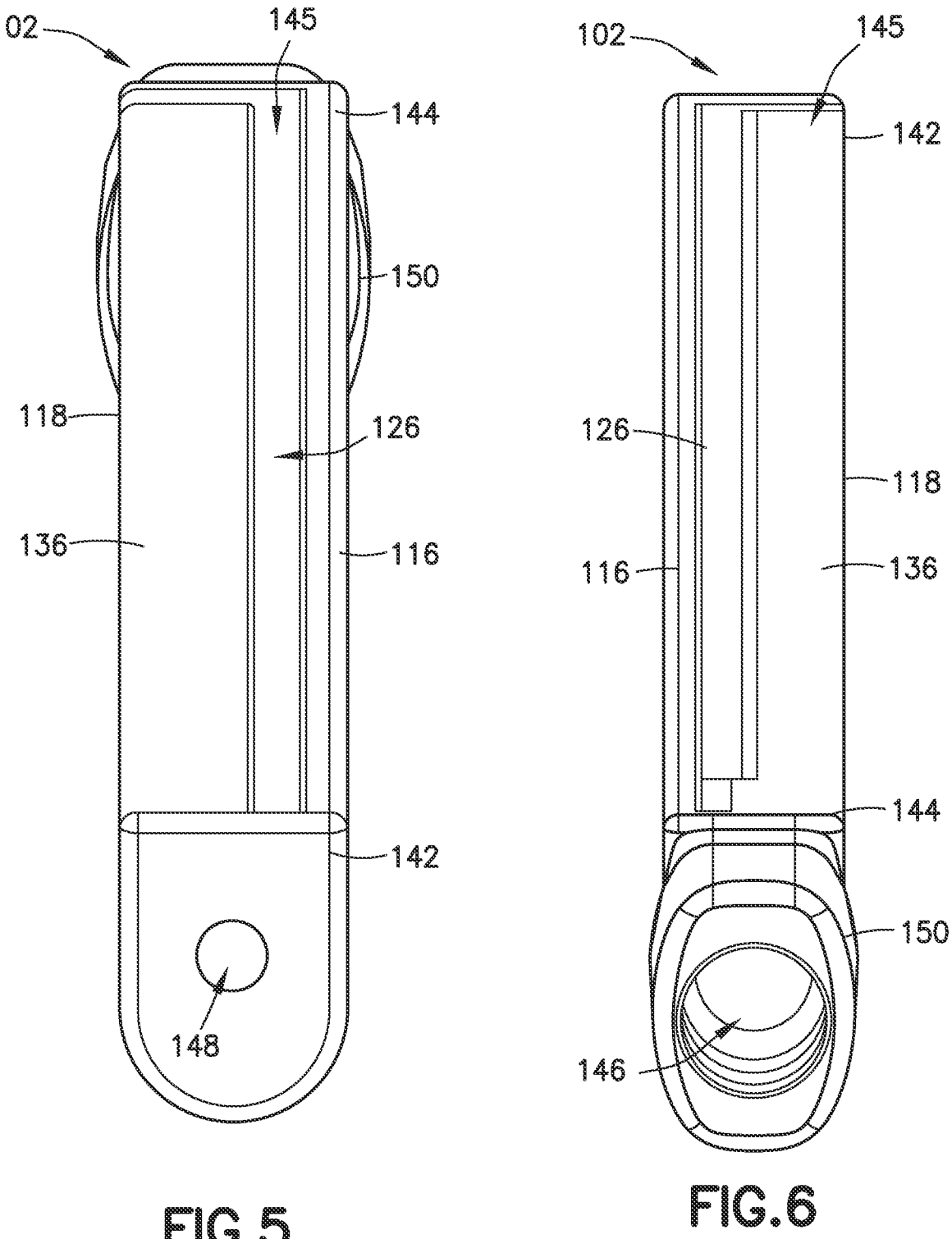
FIG. 5 is a rear perspective view of the introducer housing formed by coupling the first member illustrated in FIG. 3 to the second member illustrated in FIG. 4.
FIG. 6 is a front perspective view of the introducer housing illustrated in FIG. 5.

As shown in FIGS. 5 and 6, the first housing member 116 is configured to be coupled to the second housing member 118 to collectively form the introducer housing 114. The first housing member 116 and the second housing member 118 collectively form a proximal end portion 142 and a distal end portion 144 of the introducer housing 114 and collectively define a top surface 145 and an inner volume 146 of the introducer housing 114.

As shown in FIG. 5, the proximal end portion 142 of the introducer housing 114 defines an opening 148. Specifically, the opening 148 is collectively funned and/or defined by the notch 128 of the first housing member 116 and the notch 138 of the second housing member 118. As described in further detail herein, the opening 148 is configured to receive a portion of the secondary catheter 108, which can be moved within the opening 148 to allow for advancement of the secondary catheter 108 relative to the introducer housing 114.

As shown in FIG. 6, the distal end portion 144 of the introducer housing 114 includes and/or otherwise forms a coupler 150. In other words, the distal end portion 122 of the first housing member 116 and the distal end portion 132 of the second housing member 118 collectively form the coupler 150 at the distal end portion 144 of the introducer housing 114. The coupler 150 can be any suitable shape, size, and/or configuration. For example, the coupler 150 may form a set of threads, which can form a threaded coupling with an associated threaded portion of the lock 104, as described in further detail herein.

The lock 104 of the blood draw device 100 may be coupled to the introducer via the coupler 150, with the lock 104 configured to couple the introducer 102 to the PIVC and/or any suitable intermediate device or adapter coupled to the PIVC. In the illustrated embodiment, the lock 104 has a coupler 152, a blunted cannula 154, a first arm 156, and a second arm 158, as shown in FIG. 2, but it is recognized that the lock 104 could have an alternative construction, such as the blunted cannula 154 instead being a luer, luer slip or needle, for example. In addition, the lock 104 defines a lumen 160 extending through the coupler 152 and the blunted cannula 154. The coupler 152 is configured to couple the lock 104 to the coupler 150 of the introducer housing 114. Specifically, in this embodiment, the coupler 152 includes and/or forms one or more protrusions configured to selectively engage the threads defined and/or formed by the coupler 150 of the introducer housing 114, thereby forming a threaded coupling.

The blunted cannula 154 extends from the coupler 152 and is disposed between the first arm 156 and the second arm 158. The blunted cannula 154 can be any suitable shape, size, and/or configuration. In some embodiments, the blunted cannula 154 can have a length that is sufficient to extend through at least a portion of the PIVC or through an adapter and at least partially into or through the PIVC. Furthermore, the blunted cannula 154 can have an inner diameter (a diameter of a surface at least partially defining the lumen 160) that is similar to or slightly larger than an outer diameter of a portion of the catheter 106. Thus, the lumen 160 of the lock 104 can receive a portion of the catheter 106 when the blood draw device 100 is transitioned between the first configuration and the second configuration.

Figure 3:
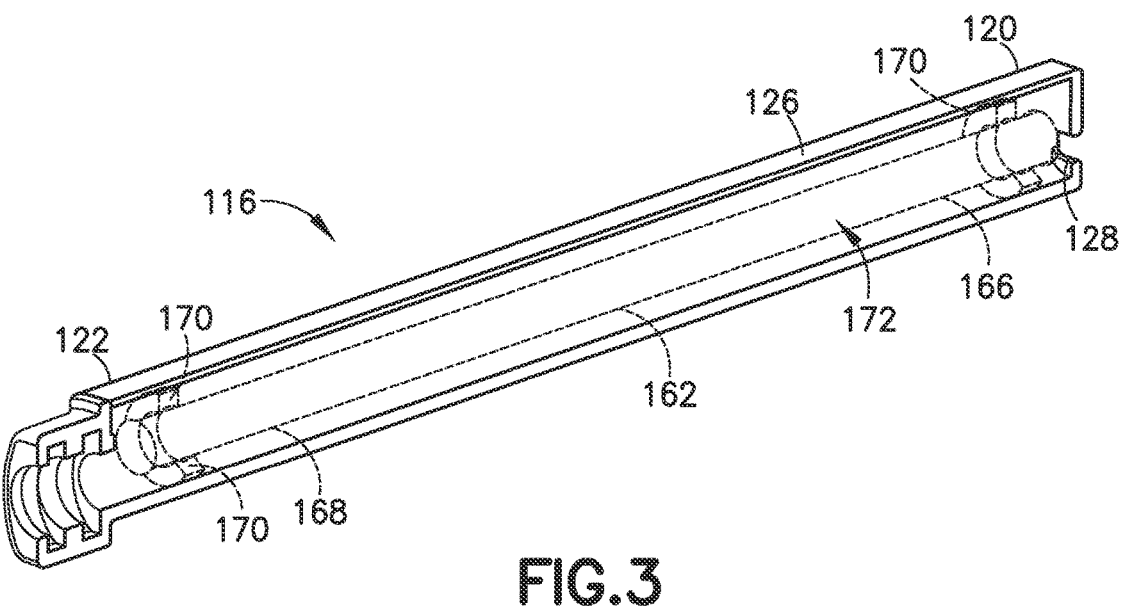
FIG. 3 is a perspective view of a first member of an introducer housing included in the blood draw device of FIG. 1.
Figure 4:
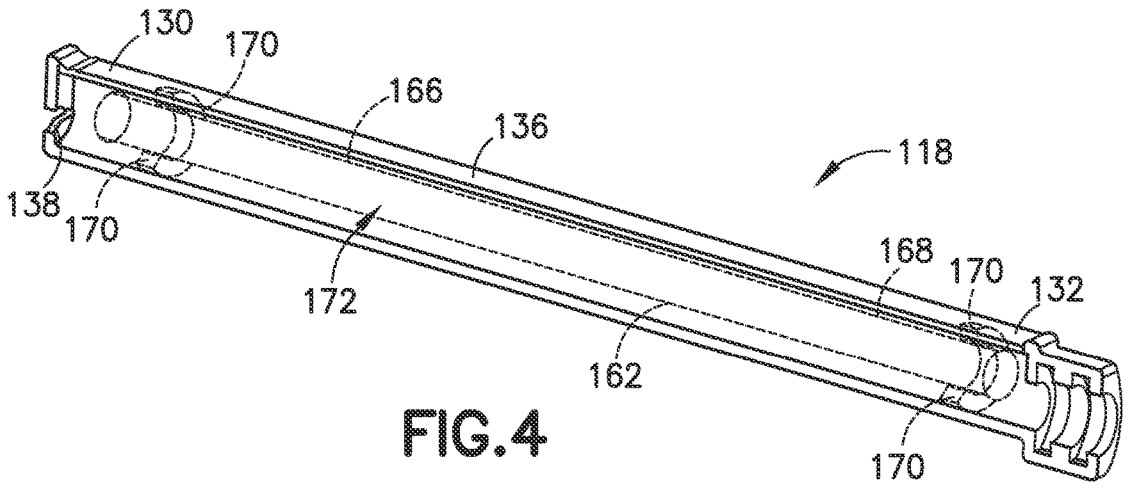
FIG. 4 is a perspective view of a second member of the introducer housing included in the blood draw device of FIG. 1.

As best shown in FIGS. 2-4, a guide tube 162 is included in the introducer 102 that is contained within the inner volume 146 of the introducer housing 114 when the first housing member 116 and the second housing member 118 are joined together. The guide tube 162 is oriented in a lengthwise direction 164 and extends between the proximal end portion 142 and the distal end portion 144 of the introducer housing 114. A proximal end 166 and distal end 168 of the guide tube 162 are supported by cradles 170 formed at the opposing ends of the introducer housing 114, on the inner surfaces 124, 134 of the first housing member 116 and the second housing member 118. The cradles 170 formed on the inner surfaces 124, 134 of the first housing member 116 and second housing member 118 are configured to hold the guide tube 162 in a fixed, secure arrangement with the introducer housing 114 and in a desired position relative to opening 148. When secured within cradles 170, the guide tube 162 is fixedly positioned relative to the introducer housing 114 and is positioned such that a centerline of the guide tube 162 (in the lengthwise direction 164) is aligned with a centerline of the opening 148 in the introducer housing 114. The guide tube 162 is sized to have a diameter greater than that of the opening 148, such that the perimeter/circumference of the opening 148 is contained within the perimeter/circumference of the guide tube 162.

According to embodiments, the guide tube 162 may be formed of a semi-rigid material that is capable of flexing or bending radially inward when a pressure is applied orthogonally to the outer surface of the guide tube 162. The guide tube 162 may thus be formed of polyurethane, silicone, or other plastics, as non-limiting examples. According to embodiments, the guide tube 162 may also be extruded with a lubricous additive or have a lubricant applied to an inner or outer surface thereof, to facilitate movement of the catheter arrangement 140 through the lumen 172 defined by the guide tube 162 ("guide lumen"), as described in further detail herein.

Figure 7A:
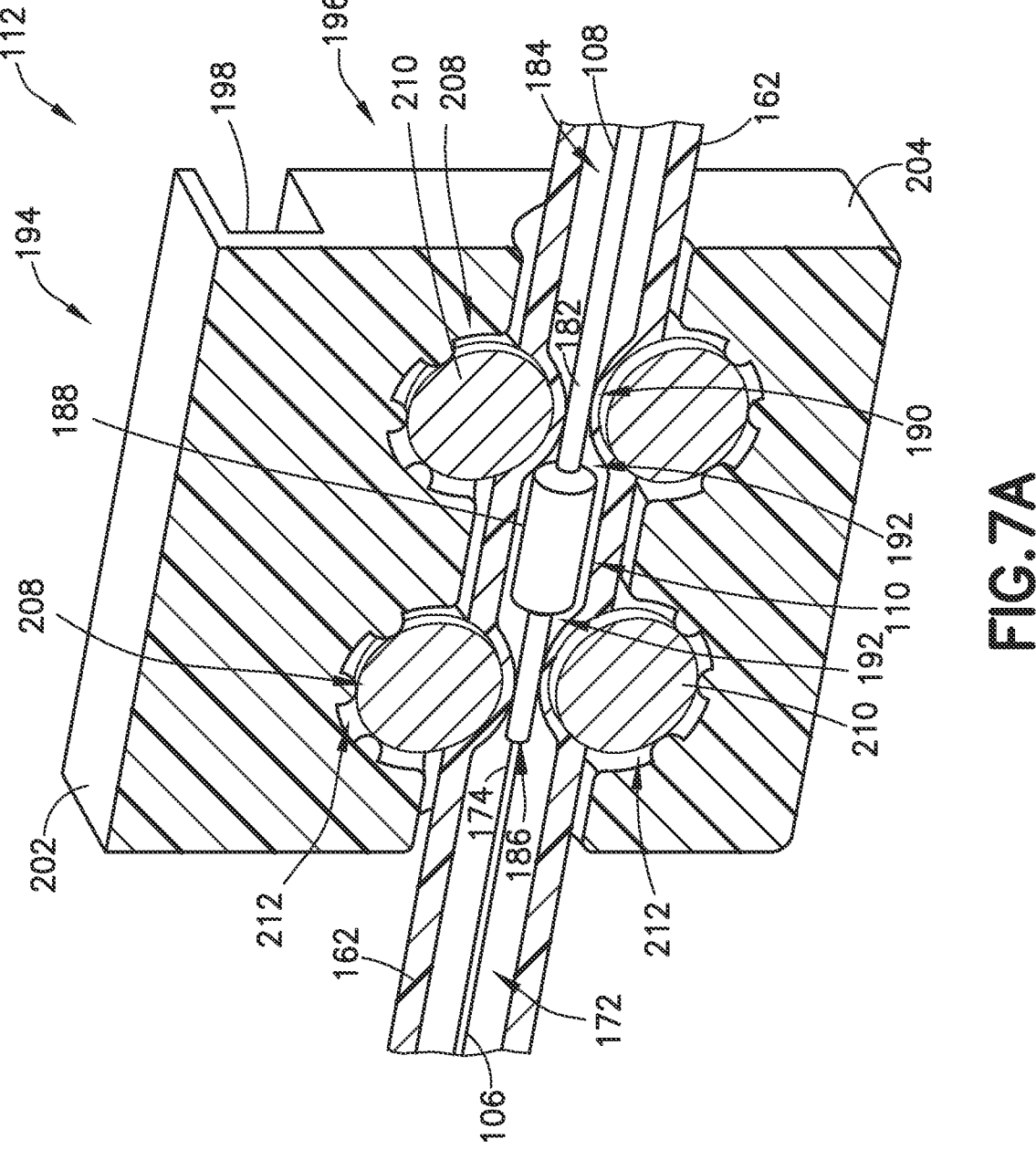
FIG. 7A is a cross-sectional view of an advancement member of the blood draw device taken along the line 7-7 in FIG. 1, according to an embodiment.
Figure 7B:
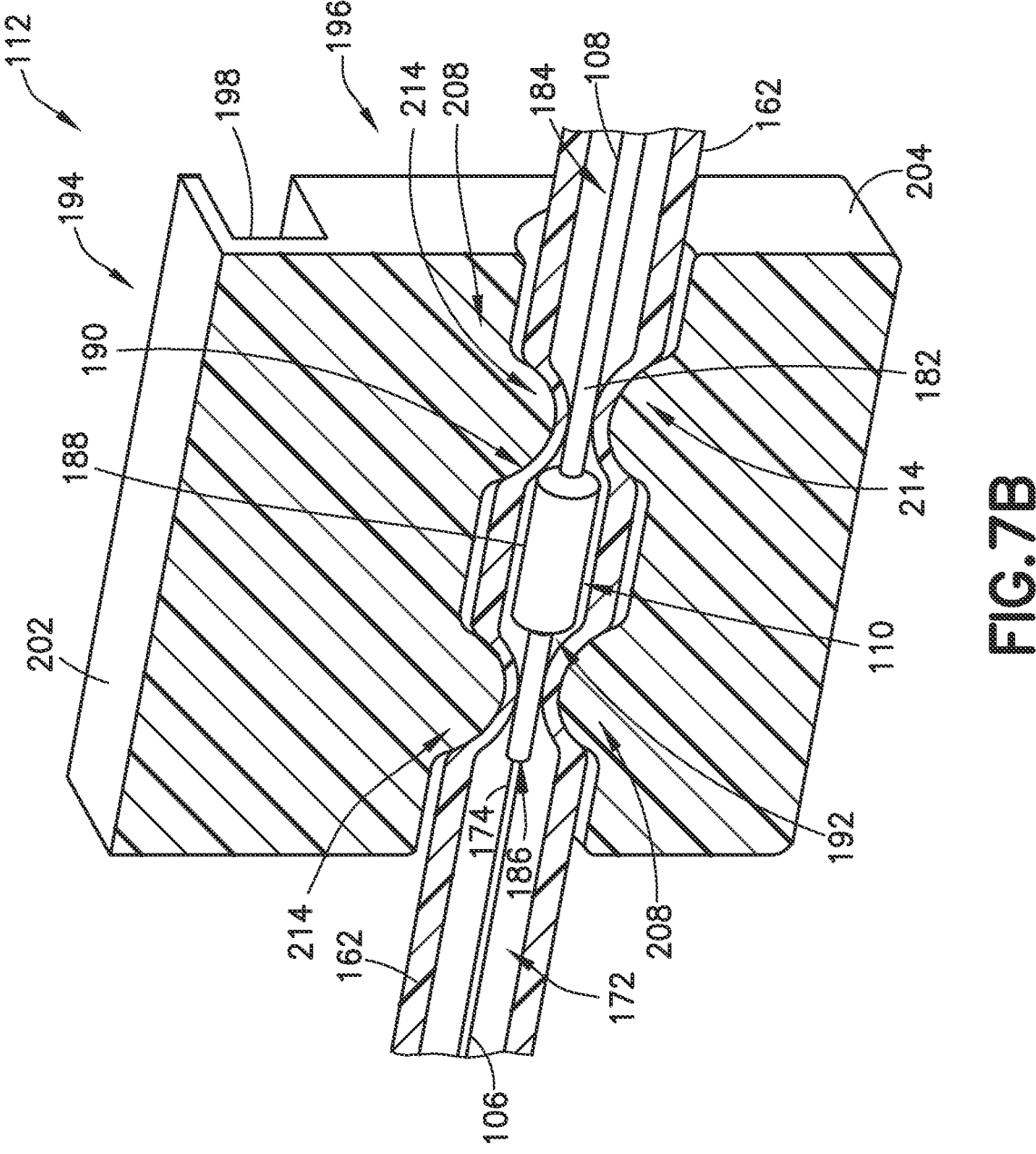
FIG. 7B is a cross-sectional view of an advancement member of the blood draw device taken along the line 7-7 in FIG. 1, according to another embodiment.

According to embodiments, at least a portion of the catheter 106, a portion of the secondary catheter 108, and the catheter fitting 110—i.e., the catheter arrangement 140—is movably disposed within the lumen 172 of guide tube 162. As shown in FIG. 2 and FIGS. 7A and 7B, the catheter 106 has a proximal end portion 174 and a distal end portion 176 and defines a lumen 178, and the secondary catheter 108 has a proximal end portion 180 and a distal end portion 182 and defines a lumen 184. The proximal end portion 174 of the catheter 106 is coupled to a first end 186 of a body 188 of catheter fitting 110, while the distal end portion 182 of the secondary catheter 108 is coupled to a second end 190 of the body 188 of catheter fitting 110. The body 188 of catheter fitting 110 is configured as a hollow structure, such that the lumen 184 of secondary catheter 108 is in fluid communication with the lumen 178 of catheter 106 by way of the catheter fitting 110.

In some embodiments, the secondary catheter 108 can have a larger diameter than the catheter 106, such that the proximal end portion 174 of the catheter 106 is at least partially disposed within the lumen 184 defined by the secondary catheter 108 when the proximal end portion 174 of the catheter 106 and the distal end portion 182 of the secondary catheter 108 are coupled to the catheter fitting 110. In some embodiments, such an arrangement can, for example, reduce and/or substantially prevent leaks associated with fluid flowing between the catheter 106 and the secondary catheter 108. In some embodiments, such an arrangement can also limit, reduce, and/or substantially prevent hemolysis of a volume of blood as the volume of blood flows through the catheter 106 and the secondary catheter 108. In this manner, when the secondary catheter 108 is coupled to a fluid reservoir, fluid source, syringe, evacuated container, or pump (via a coupler 191 provided at the proximal end 180 of the secondary catheter 108), the secondary catheter 108 establishes fluid communication between the reservoir, source, pump, etc. and the catheter 106. Additionally, in some embodiments, the secondary catheter 108 may also have a clamp (not shown) provided thereon, such as a slide clamp or pinch clamp, to facilitate stoppage of flow through the secondary catheter 108.

According to embodiments, the body 188 of catheter fitting 110 also includes thereon a plurality of seats 192 that provide for advancement of the catheter fitting 110 through the guide tube 162 when engaged by the advancement member 112 (through guide tube 162), as described in further detail herein. The seats 192 may be formed as recesses or other surface features that may be engaged by the advancement member 112 to provide a solid engagement point therebetween.

As described in further detail herein, a portion of the advancement member 112 is configured to be advanced along the top surface 145 of the introducer housing 114 as a user moves the advancement member 112 relative to the introducer housing 114. Movement of the advancement member 112 distally along the introducer housing 114 facilitates the advancing of the catheter arrangement 140 through a portion of the blood draw device 100, such that the catheter 106 may be advanced into a portion of the MC and/or a portion of the vasculature. That is, the advancement member 112 can be moved relative to the introducer housing 114 to move the catheter 106 between a first position, in which the catheter 106 is disposed within the introducer housing 114 (e.g., the entire catheter 106 is disposed within the inner volume 146 of introducer housing 114 or within the introducer housing 114 and the lock 104) and a second position, in which the distal end portion 176 of the catheter 106 is at least partially disposed in a position distal to the lock 104 and/or the PIV (not shown) when the lock 104 is coupled to the PIV.

Figure 8:
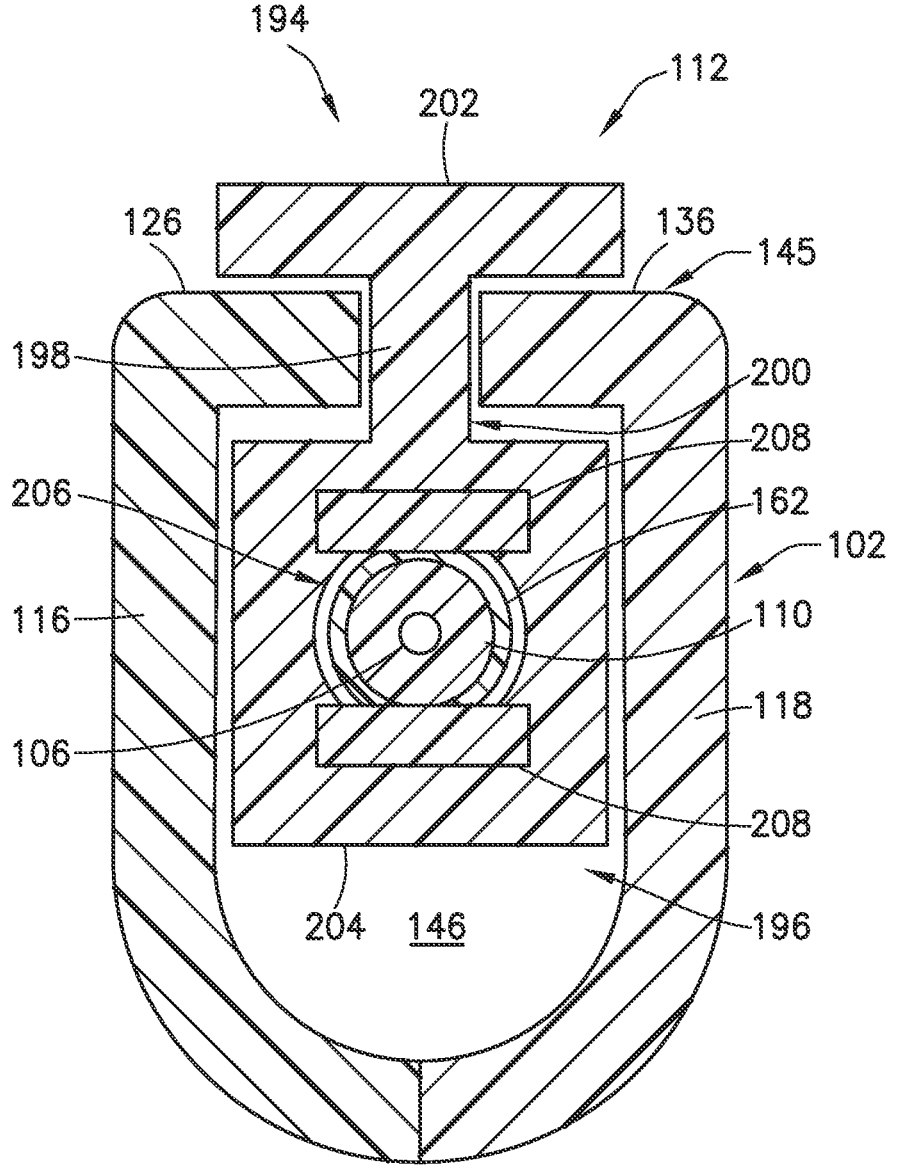
FIG. 8 is a cross-sectional view of a portion of blood draw device taken along the line 8-8 in FIG. 1, according to an embodiment.

Construction of the advancement member 112, and positioning thereof within introducer housing 114, is shown in greater detail in FIGS. 7A and 7B and FIG. 8, according to embodiments. The advancement member 112 may generally be characterized as including a first portion 194, a second portion 196, and a connecting portion 198 extending therebetween. The first portion 194 of the advancement member 112 is disposed on the top surface 145 of the introducer housing 114 and the second portion 196 of the advancement member 112 is disposed within the inner volume 146. The connecting portion 198 extends downward from first portion 194 and connects to the second portion 196, to join the first and second portions together. The connecting portion 198 is slotted within a track 200 formed in the top surface 145 of the introducer housing 114 (i.e., in a track 200 formed between the top surface 126 of first housing member 116 and the top surface 145 of second housing member 118) and slides within the track 200 when a user engages the first portion 194 to move the advancement member 112 relative to the introducer housing 114.

According to an embodiment, the first portion 194 of the advancement member 112 is configured as a tab 202 that can be engaged and/or manipulated by a user (e.g., by a finger or thumb of the user) to move the advancement member 112 relative to the introducer housing 114. According to embodiments, the tab 202 may be rounded or flat on top and may include a set of ridges and/or any suitable surface finish that can, for example, increase the ergonomics of the advancement member 112 and/or blood draw device 100.

The second portion 196 of the advancement member 112 is a main body 204 positioned within the inner volume 146 defined by the introducer housing 114. The main body 204 can be any suitable shape, size, and/or configuration that provides for a smooth translation of the advancement member 112 relative to the introducer housing 114, and may thus have a size and shape that is associated with and/or based at least in part on a size and/or shape of the introducer housing 114. The main body 204 includes a channel 206 formed therethrough that extends in the lengthwise direction 164. The channel 206 is sized to receive the guide tube 162 therein, and thus a diameter of the channel 206 is at least slightly larger than the diameter of the guide tube 162.

An arrangement of pinch members 208 is integrated with (or positioned relative to) the main body 204 so as to extend radially inward, into the channel 206. The pinch members 208 are configured to provide localized compression to the guide tube 162 and to engage with one or more features of the catheter fitting 110 (e.g., seats 192) through the guide tube 162, so as to provide for advancement of the catheter 106 (as part of catheter arrangement 140) without any direct contact between the advancement member 112 and the catheter fitting 110 that is coupled to the catheter 106. The pinch members 208 may be provided as, rollers, bearings, low-friction sliding surfaces (e.g., a low-friction material and/or with lubricant added thereto), or the like, and may be rounded, angled, spherical, or cylindrical, according to embodiments, with it understood that the pinch members 208 should provide for a smooth translation and sliding of the advancement member along guide tube 162 with minimal friction therebetween.

In order to provide localized compression of the guide tube 162 at areas engaged by the pinch members 208, a portion of the pinch members are positioned above the guide tube 162 (and catheter fitting 110) and a portion of the pinch members are positioned below the guide tube 162 (and catheter fitting 110)— with a vertical distance between the pinch members 208 that oppose each other being less than an outer diameter of the guide tube 162. As the pinch members 208 move lengthwise along the guide tube 162 during movement of the advancement member 112, the pinch members 208 maintain contact with the guide tube 162 and apply localized compression thereto that cause the guide tube 162 to flex or bend radially inwardly.

In addition to being positioned both above and below the catheter fitting 110, the pinch members 208 are also positioned on opposing ends of the catheter fitting 110. That is, a portion of the pinch members 208 is positioned distally from the catheter fitting 110, adjacent the first end 186 thereof, and another portion of the pinch members 208 is positioned proximally from the catheter fitting 110, adjacent the second end 190 thereof, such that the catheter fitting 110 is trapped by the pinch members 208. With the catheter fitting 110 trapped between the pinch members 208, any movement of the advancement member 112 relative to the introducer housing 114 will cause a corresponding movement of the catheter arrangement 140 relative to the introducer housing 114.

In some embodiments, as illustrated in FIG. 7A, the pinch members 208 are provided as bearings 210 that are seated within recesses or cavities 212 formed in the main body 204 and that extend into the channel 206 to pinch the guide tube 162. As one example, an arrangement of four cylindrical bearings 210 may be provided in the advancement member 112, with a first pair of the cylindrical bearings 210 positioned adjacent the first end 186 of the catheter fitting 110, above and below the catheter fitting 110, and with a second pair of the cylindrical bearings 210 positioned adjacent the second end 190 of the catheter fitting 110, above and below the catheter fitting 110. The bearings 210 align with the seats 192 formed on catheter fitting 110 to properly engage the catheter fitting 110, through the guide tube 162, to facilitate smooth translation of the catheter arrangement 140.

In some embodiments, as illustrated in FIG. 7B, the pinch members 208 are provided as a plurality of protrusions 214 that are integrally formed with the main body 204 and that extend into the channel 206 to pinch the guide tube 162. As one example, an arrangement of four cylindrical protrusions 214 may be provided on the main body 204, with a first pair of the cylindrical protrusions 214 positioned adjacent the first end 186 of the catheter fitting 110, above and below the catheter fitting 110, and with a second pair of the cylindrical protrusions 214 positioned adjacent the second end 190 of the catheter fitting 110, above and below the catheter fitting 110. The protrusions 214 align with the seats 192 formed on catheter fitting 110 to properly engage the catheter fitting 110, through the guide tube 162, to facilitate smooth translation of the catheter arrangement 140.

Figures 9, 10:
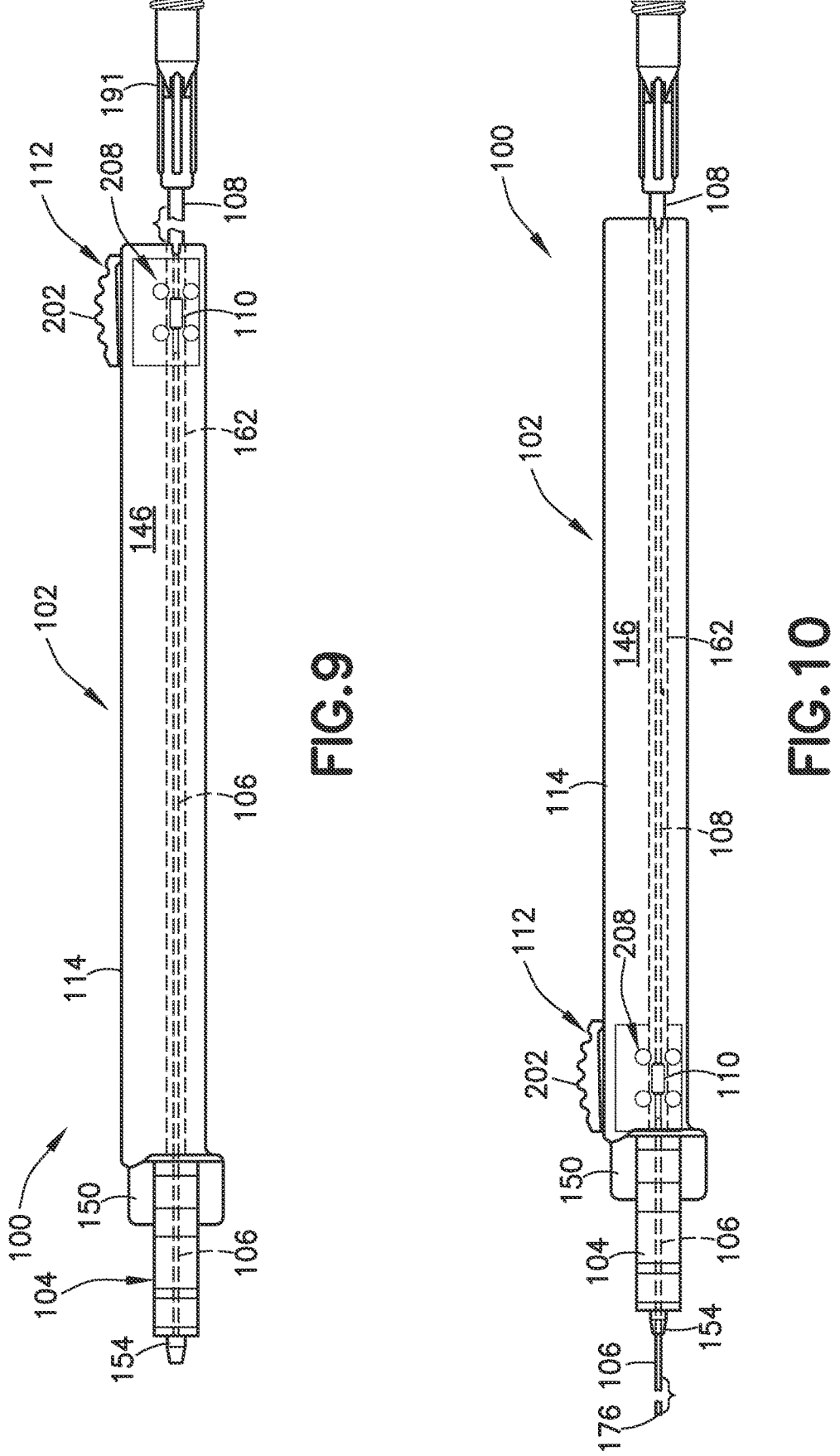
FIG. 9 is a side sectional view of the blood draw device of FIG. 1 first configuration.
FIG. 10 is a side sectional view of the blood draw device of FIG. 1 in a second configuration.

Referring now to FIGS. 9 and 10, changing of the blood draw device 100 between the first configuration and second configuration is shown. The blood draw device 100 can be in the first configuration prior to use and can be transitioned by a user (e.g., a doctor, physician, nurse, technician, phlebotomist, and/or the like) from the first configuration (FIG. 9) to the second configuration (FIG. 10) to dispose at least the distal end portion 176 of the catheter 106 in a distal position relative to the introducer housing 114 (e.g., within an indwelling PIV (not shown) or distal to the indwelling PIV).

The blood draw device 100 is in the first configuration of FIG. 9 when the catheter 106 is disposed in the first position within the introducer housing 114. In some embodiments, substantially the entire catheter 106 is disposed within the introducer housing 114 when the catheter 106 is in the first position. In other embodiments, the catheter 106 is disposed within the introducer housing 114 and the lock 104 when catheter 106 is in the first position.

The advancement member 112 is disposed in a proximal position when the blood draw device 100 is in the first configuration, and the user may engage the tab 202 of advancement member 112 to move the advancement member 112 relative to the introducer housing 114, which in turn, moves the catheter 106 (as part of catheter arrangement 140) from the first position (e.g., disposed within the introducer housing 114) toward the second position. That is, as explained previously, pinch members 208 of the advancement member 112 deflect and pinch through guide tube 162 to engage with the catheter fitting 110 (i.e., seats 192 on catheter fitting 110, FIGS. 7A and 7B) to enable movement of the catheter arrangement 140 within guide tube and relative to introducer housing 114. In this manner, the catheter 106 is moved through the inner volume 146 and the lumen 160 of the lock 104 and, as such, at least the distal end portion 176 of the catheter 106 is disposed outside of and distal to the lock 104.

The blood draw device 100 is in the second configuration of FIG. 10 when the catheter 106 is disposed in the second position. The second position of the catheter 106 is reached when the distal end portion 176 of the catheter 106 is placed in a desired position relative to a distal end portion of the PIVC. In some instances, for example, a distal end of the catheter 106 can be substantially flush with a distal end of the PIVC when the catheter 106 is in the second position. In other instances, the distal end of the catheter 106 can extend a predetermined distance beyond the distal end of the PIVC (e.g., distal to the distal end of the PIVC), such that the distal surface of the catheter 106 is positioned within the vein at a predetermined distance beyond the distal surface of the catheter 106 (e.g., a position within a vein that is substantially free from debris (e.g., fibrin/blood clots) otherwise surrounding the distal end portion of the PIVC).

With the catheter 106 in the second position (e.g., with the blood draw device 100 in the second configuration shown, for example, in FIG. 12), the user can establish fluid communication between a fluid reservoir, fluid source, syringe, and/or the like and the catheter 106. The blood draw device 100 can then aspirate a volume of blood from the vein based at least in part on disposing the distal surface of the catheter 106 at the predetermined and/or desired distance beyond the distal surface of the PIVC. In some instances, once a desired amount of blood has been collected and/or once a desired volume of a drug has been delivered to the patient, the user can move the advancement member 112 in the proximal direction, such as moving the advancement member 112 back to its proximal most position, so as to move the catheter 106 back to the first position.

Beneficially, embodiments of the blood draw device as described herein provide a means for advancing a catheter into a PIVC and a patient's vasculature in a non-contact manner. A guide tube is positioned within the introducer housing to provide a lumen within which a catheter arrangement can travel. An advancement member rides along the outer surface of the guide tube and engages the catheter arrangement, through the guide tube, to provide for advancement of the catheter arrangement. The catheter arrangement is supported by the guide tube as it advances through the introducer housing, such that the catheter is prevented from bending, kinking, and/or deforming during advancement. The guide tube also provides a barrier to the potential introduction of microbes into the fluid path of the blood draw device and the PIVC, thereby reducing the chances for CRBSIs.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A blood draw device for use with a peripheral intravenous catheter (PIVC) comprising:
an introducer comprising:
a housing extending in a lengthwise direction between a proximal end and a distal end; and
a guide tube fixedly contained within the housing and extending in the lengthwise direction, the guide tube defining a guide lumen;
a catheter arrangement moveable within the guide lumen, the catheter arrangement comprising:
a catheter defining a first catheter lumen and having a proximal end and a distal end;
a secondary catheter defining a second catheter lumen and having a proximal end and a distal end; and
a catheter fitting coupled between the proximal end of the catheter and the distal end of the secondary catheter, to fluidly connect the first and second catheter lumens; and
an advancement member coupled to the introducer and moveable in the lengthwise direction, the advancement member comprising an arrangement of pinch members positioned within the housing that is configured to pinch the guide tube and to move along the guide tube when the advancement member is moved;

wherein, in response to moving the advancement member distally along the housing, the arrangement of pinch members push the catheter fitting distally within the guide lumen, such that the catheter and secondary catheter are also advanced distally.

2. The blood draw device of claim 1, wherein the advancement member comprises:

a push tab positioned on an outer surface of the housing and actuatable by a user to move in the lengthwise direction; and a main body joined to the push tab via a connecting portion, the main body positioned within an interior volume of the housing and including a channel formed therethrough to receive the guide tube, wherein the arrangement of pinch members is integrated with the main body;

wherein the connecting portion is seated within a groove in the housing that extends in the lengthwise direction, and wherein the connecting portion is slideable within the groove to enable movement of the advancement member in the lengthwise direction.

3. The blood draw device of claim 2, wherein the arrangement of pinch members comprises a plurality of bearings seated within recesses or cavities formed in the main body, the plurality of bearings extending into the channel to pinch the guide tube.

4. The blood draw device of claim 2, wherein the arrangement of pinch members comprises a plurality of protrusions formed as part of the main body and that extend into channel to pinch the guide tube, the plurality of protrusions comprising spherical or cylindrical protrusions.

5. The blood draw device of claim 1, wherein the arrangement of pinch members is configured such that at least one pinch member of the arrangement of pinch members is positioned on each of opposing ends of the catheter fitting, to trap the catheter fitting therebetween.

6. The blood draw device of claim 1, wherein the guide tube comprises a flexible material that deflects or bends when pinched by the arrangement of pinch members.

7. The blood draw device of claim 1, wherein the guide tube comprises a lubricant applied to the guide lumen, to facilitate movement of the catheter arrangement within the guide lumen.

8. The blood draw device of claim 1, wherein the guide tube supports movement of the catheter arrangement through the guide lumen along a full length of the housing during lengthwise movement of the advancement member, so as to prevent kinking of the catheter.

9. The blood draw device of claim 1, wherein the catheter fitting comprises a fitting body having a first end engageable with the proximal end of the catheter and a second end engageable with the distal end of the secondary catheter, the fitting body comprising a hollow structure that enables fluid flow between the catheter and the secondary catheter; and wherein the fitting body comprises a plurality of seats that engage the arrangement of pinch members, through the guide tube, such that the catheter fitting is pushed within the guide lumen in response to movement of the advancement member along the housing.

10. The blood draw device of claim 1, wherein the housing comprises an end wall at the proximal end of the housing, the end wall including an opening formed therein that receives the secondary catheter and provides for movement of the secondary catheter relative to the housing.

11. The blood draw device of claim 1, wherein the catheter and secondary catheter are advanced distally, via the arrangement of pinch members pushing the catheter fitting within the guide lumen, without direct contact between the advancement member and the catheter arrangement.

12. The blood draw device of claim 1, wherein in response to moving the advancement member proximally along the housing, the arrangement of pinch members push the catheter fitting proximally within the guide lumen, such that the catheter and secondary catheter are also retracted proximally.

13. A blood draw device for use with a peripheral intravenous catheter (PIVC) comprising:

an introducer comprising:

a housing extending in a lengthwise direction between a proximal end and a distal end; and a guide tube fixedly contained within the housing and extending in the lengthwise direction, the guide tube defining a guide lumen;

a catheter arrangement moveable within the guide lumen, the catheter arrangement comprising:

a catheter defining a first catheter lumen and having a proximal end and a distal end;

a secondary catheter defining a second catheter lumen and having a proximal end and a distal end; and a catheter fitting coupled between the proximal end of the catheter and the distal end of the secondary catheter, to fluidly connect the first and second catheter lumens; and an advancement member configured to move along the housing in the lengthwise direction and, responsive to such movement, distally advance or proximally retract the catheter arrangement in a contactless manner;

wherein the advancement member comprises an arrangement of pinch members positioned within the housing that are configured to pinch the guide tube and to push the catheter fitting within the guide lumen when the advancement member is moved, thereby distally advancing or proximally retracting the catheter and the secondary catheter.

14. The blood draw device of claim 13, wherein the arrangement of pinch members is configured such that at least one pinch member of the arrangement of pinch members is positioned on each of opposing ends of the catheter fitting, to trap the catheter fitting therebetween.

15. The blood draw device of claim 13, wherein the advancement member comprises:

a push tab positioned on an outer surface of the housing and actuatable by a user to move in the lengthwise direction; and a main body joined to the push tab via a connecting portion, the main body positioned within an interior volume of the housing and including a channel formed there through to receive the guide tube, wherein the arrangement of pinch members is integrated with the main body;

wherein the connecting portion is seated within a groove in the housing that extends in the lengthwise direction, and wherein the connecting portion is slideable within the groove to enable movement of the advancement member in the lengthwise direction.

16. The blood draw device of claim 15, wherein the arrangement of pinch members comprises a plurality of bearings seated within recesses or cavities formed in the main body, the plurality of bearings extending into the channel to pinch the guide tube.

17. The blood draw device of claim 15, wherein the arrangement of pinch members comprises a plurality of protrusions formed integrally with the main body and that extend into the channel to pinch the guide tube, the plurality of protrusions comprising spherical or cylindrical protrusion.

18. The blood draw device of claim 13, wherein the catheter fitting comprises a fitting body having a first end engageable with the proximal end of the catheter and a second end engageable with the distal end of the secondary catheter, the fitting body comprising a hollow structure that enables fluid flow between the catheter and the secondary catheter; and wherein the fitting body comprises a plurality of seats that engage the arrangement of pinch members, through the guide tube, such that the catheter fitting is pushed within the guide lumen in response to movement of the advancement member along the housing.

19. The blood draw device of claim 13, wherein the guide tube comprises a lubricant applied to the guide lumen, to facilitate movement of the catheter arrangement within the guide lumen.

20. The blood draw device of claim 13, wherein the guide tube supports movement of the catheter arrangement through the guide lumen along a full length of the housing during lengthwise movement of the advancement member, so as to prevent kinking of the catheter during advancing or retracting thereof.

* * * * *